United States Patent
Matsubayashi et al.

(10) Patent No.: US 12,338,424 B2
(45) Date of Patent: Jun. 24, 2025

(54) CELL STRUCTURE CONNECTION METHOD AND CONNECTION SUPPORT DEVICE

(71) Applicant: CYFUSE BIOMEDICAL K.K., Tokyo (JP)

(72) Inventors: Kumika Matsubayashi, Fukuoka (JP); Yasuto Kishii, Tokyo (JP)

(73) Assignee: CYFUSE BIOMEDICAL K.K., Tokyo (JP)

( * ) Notice: Subject to any disclaimer, the term of this patent is extended or adjusted under 35 U.S.C. 154(b) by 1271 days.

(21) Appl. No.: 17/046,264

(22) PCT Filed: Apr. 9, 2018

(86) PCT No.: PCT/JP2018/014891
§ 371 (c)(1),
(2) Date: Oct. 8, 2020

(87) PCT Pub. No.: WO2019/198124
PCT Pub. Date: Oct. 17, 2019

(65) Prior Publication Data
US 2021/0079333 A1    Mar. 18, 2021

(51) Int. Cl.
| | |
|---|---|
| C12M 1/12 | (2006.01) |
| C12M 1/00 | (2006.01) |
| C12M 1/04 | (2006.01) |
| C12M 1/26 | (2006.01) |
| C12M 3/00 | (2006.01) |
| C12N 5/00 | (2006.01) |

(52) U.S. Cl.
CPC ............ *C12M 25/10* (2013.01); *C12M 21/08* (2013.01); *C12M 23/06* (2013.01); *C12M 23/24* (2013.01); *C12M 23/44* (2013.01); *C12M 23/50* (2013.01); *C12M 33/00* (2013.01); *C12N 5/0068* (2013.01); *C12N 2533/30* (2013.01)

(58) Field of Classification Search
CPC ...... C12M 25/10; C12M 21/08; C12M 23/06; C12M 23/24; C12M 23/44; C12M 23/50; C12M 33/00; C12M 23/40; C12M 23/46; C12M 25/14; C12M 23/20; C12N 5/0068; C12N 2533/30; C12N 5/0697
See application file for complete search history.

(56) References Cited

U.S. PATENT DOCUMENTS

| | | | |
|---|---|---|---|
| 8,198,086 B2 | 6/2012 | Koga et al. | |
| 2011/0033927 A1 | 2/2011 | Rolle et al. | |
| 2017/0342373 A1 | 11/2017 | Wan et al. | |
| 2019/0040359 A1 | 2/2019 | Nakayama et al. | |

FOREIGN PATENT DOCUMENTS

| | | | | |
|---|---|---|---|---|
| DE | 10 2005 001 747 A1 | 7/2006 | | |
| JP | 2006345778 A | * 12/2006 | ............ | C12M 29/16 |
| JP | 4517125 B2 | 8/2010 | | |
| JP | 2013-529081 A | 7/2013 | | |
| WO | WO 2010/115187 A1 | 10/2010 | | |
| WO | WO 2011/146046 A1 | 11/2011 | | |
| WO | WO 2017/100782 A1 | 6/2017 | | |
| WO | WO 2017/131241 A1 | 8/2017 | | |

OTHER PUBLICATIONS

Callanan et al., "Development of a rotational cell-seeding system for tubularized extracellular matrix (ECM) scaffolds in vascular surgery", 2013 Wiley Periodicals, Inc., Journal of Biomedical Materials Research B, Applied Biomaterials, May 2014, vol. 102B, Issue 4, pp. 781-788.
International Search Report for PCT/JP2018/014891 (PCT/ISA/210) mailed on Jun. 5, 2018.
Jung et al., "Scaffold-free, Human Mesenchymal Stem Cell-Based Tissue Engineered Blood Vessels", Scientific Reports, vol. 5, Art. No. 15116, Oct. 12, 2015, pp. 1-9.
Zhang et al., "Dynamic culture conditions to generate silk-based tissue-engineered vascular grafts", Biomaterials, 2009, vol. 30, pp. 3213-3223.
Extended European Search Report issued Mar. 19, 2021, in European Patent Application No. 18914260.7.
International Preliminary Report on Patentability and Written Opinion mailed Oct. 22, 2020; in PCT/JP2018/014891 (Forms PCT/IB/326, PCT/IB/373, and PCT/ISA/237).

* cited by examiner

*Primary Examiner* — Titilayo Moloye
(74) *Attorney, Agent, or Firm* — Birch, Stewart, Kolasch & Birch, LLP

(57) ABSTRACT

The connection support device includes a rod-shaped member insertable into respective hollow portions of two or more cell structures, the rod-shaped member being inserted into the hollow portions, the rod-shaped member including a circular cross section having an outer diameter capable of adhering to inner surfaces of the cell structures when the rod-shaped member contracts after maturing, and a total length longer than a sum of respective lengths of the two or more cell structures, and two presser devices including clamp portions capable of being fixed to the rod-shaped member by clamping and fitting to the rod-shaped member, the rod-shaped member being made of a material with oxygen permeability.

14 Claims, 8 Drawing Sheets

CELL STRUCTURE CONNECTION METHOD AND CONNECTION SUPPORT DEVICE

TECHNICAL FIELD

The present invention relates to a connection method and a connection support device for connecting two or more tubular cell structures including hollow portions inside.

BACKGROUND ART

Conventionally, as disclosed in PTL 1, a technique has been known that produces a three-dimensional structure by utilizing the characteristic that cell aggregates contacting each other in an adjacent manner are fused to each other, and three-dimensionally stacking the cell aggregates (spheroids) so that cell aggregates are adjacent to each other, by utilizing a support body formed by a plurality of needle-like bodies fixed in advance to extend in the normal direction of a substrate.

In this technique, the technique is disclosed that extracts cell aggregates 51, and sticks each of the cell aggregates 51 to each of the needle-like bodies of the support body to manufacture the state where the cell aggregates are skewered. For example, as a cell structure 5 for blood vessel, needle-like bodies are arranged in a tubular shape, and the cell aggregates 51 are stuck to each of the needle-like bodies. Then, when cultivated for a certain time period, as shown in FIG. 7B, the adjacent cell aggregates 51 are fused to each other, and the tubular cell structure 5 is formed on the needle-like bodies 52. Then, as shown in FIG. 7C, when the cell structure 5 is pulled out from the needle-like bodies, the tubular cell structure 5 including a hollow portion inside the tube having a length L can be extracted.

CITATION LIST

Patent Literature

PTL 1: Specification of Japanese Patent No. 4517125

SUMMARY OF INVENTION

Technical Problem

In this technique, in order to increase the length L of the tubular cell structure 5, the length of the needle-like body 52 will be increased, and the number of the cell aggregates 51 stuck to it will be increased. However, there are limitations to the technique of increasing the length of the needle-like body 52, since when the length of the needle-like body 52 is increased, there are problems of the straightness of the needle-like body 52, and the parallelism to the adjacent needle-like body 52, or due to manufacturing problems.

Therefore, a method and an apparatus that can increase the length L of the cell structure 5, without increasing the length of the needle-like body 52, are required.

The present invention has been made in view of these problems, and provides a method and a connection support device that can easily increase the length L of the cell structure 5.

Solution to Problem

It is solved by a connection support device for connecting two or more tubular cell structures by maturing the cell structures through cultivation for a predetermined time period, each of the cell structures having a hollow portion inside the each of the cell structures, the connection support device including a rod-shaped member insertable into the hollow portion of the each of the two or more cell structures, the rod-shaped member being inserted into the hollow portions, the rod-shaped member including a circular cross section having an outer diameter closely contactable to inner surfaces of the tubular cell structures by shrinkage of the rod-shaped member after the maturing, and a total length longer than a sum of respective lengths of the two or more cell structures; and two presser devices each including a clamp portion capable of being fixed to the rod-shaped member by clamping and fitting to the rod-shaped member, wherein the rod-shaped member is made of a material with oxygen permeability, and wherein in each of the two presser devices, in a case where the rod-shaped member is inserted into the two or more cell structures in a state where one ends of the two or more cell structures contacts with each other, each of the clamp portions makes a contact with each of end surfaces of another ends of the two or more cell structures that are not in a contact state.

It is solved by a connection support device for connecting two or more tubular cell structures by maturing the cell structures through cultivation for a predetermined time period, each of the cell structures having a hollow portion inside the each of the cell structures, the connection support device including a rod-shaped member insertable into the hollow portion of the each of the two or more cell structures, the rod-shaped member being inserted into the hollow portions, the rod-shaped member including a circular cross section having an outer diameter closely contactable to inner surfaces of the tubular cell structures by shrinkage of the rod-shaped member after the maturing, and a total length longer than a sum of respective lengths of the two or more cell structures, and a presser device including a clamp portion capable of being fixed to the rod-shaped member by clamping and fitting to the rod-shaped member, the rod-shaped member including a conduit through which a culture solution flows along an axial direction of the rod-shaped member from one end to the other end of the rod-shaped member, the presser device including a projection, in a case where the rod-shaped member is inserted into the two or more cell structures in a state where one ends of the two or more cell structures contacts with each other, the projection arranged along a circumference contacting an end surface of one of another ends of the two or more cell structures that are not in a contact state, the rod-shaped member being made of a material with oxygen permeability, and at the other of the both ends of the cell structures that are not in the contact state, the presser device contacting an end surface of the other end.

It is solved by a cell structure connection method for connecting two or more tubular cell structures with a rod-shaped member made of a material with oxygen permeability, each of the two or more tubular cell structures including a hollow portion inside, with a rod-shaped member having a conduit inside the each of the cell structures, the rod-shaped member having a conduit penetrating along an axial direction of the rod-shaped member from one end to another end of the rod-shaped member, the rod-shaped member being made of a material with oxygen permeability, the rod-shaped member having a total length longer than a sum of respective lengths of the two or more cell structures, wherein the cell structure connection method includes an insertion step of inserting the rod-shaped member into the hollow portion of the each of the two or more cell structures, a fixing step of fixing the two or more cell structures to the rod-shaped member with two presser devices each of which includes a clamp portion capable of being fixed to the rod-shaped member and has an inner diameter substantially a same as an outer diameter of a cross section of the rod-shaped member, wherein in each of the two presser devices, in a case where the rod-shaped member is inserted into the two or more cell structures in a state where one ends of the two or more cell structures contacts with each other, each of the clamp portions makes a contact with each of end surfaces of another ends of the two or more cell structures that are not in a contact state, so that the two presser devices contacts the one ends of the two or more cell structures that contact with each other, a maturing step of cultivating and maturing the two or more cell structures by flowing a culture solution into the conduit of the rod-shaped member.

It is solved by a cell structure connection method for connecting two or more tubular cell structures with a rod-shaped member made of a material with oxygen permeability, each of the two or more tubular cell structures including a hollow portion inside, with a rod-shaped member having a conduit inside the each of the cell structures, the rod-shaped member having a conduit penetrating along an axial direction of the rod-shaped member from one end to another end of the rod-shaped member, the rod-shaped member being made of a material with oxygen permeability, the rod-shaped member having a total length longer than a sum of respective lengths of the two or more cell structures, wherein the cell structure connection method includes an insertion step of inserting the rod-shaped member into the hollow portion of the each of the two or more cell structures, a fixing step of fixing the two or more cell structures to the rod-shaped member with a presser device which includes a clamp portion capable of being fixed to the rod-shaped member and has an inner diameter substantially a same as an outer diameter of a cross section of the rod-shaped member, the presser device including a projection, in a case where the rod-shaped member is inserted into the two or more cell structures in a state where one ends of the two or more cell structures contacts with each other, the projection arranged along a circumference contacting an end surface of one of another ends of the two or more cell structures that are not in a contact state, so that the presser devices contacts the one ends of the two or more cell structures that contact with each other, a fixing step of fixing the two or more cell structures to the rod-shaped member by causing, at one of both ends of the cell structures that are not in a contact state when one ends of the cell structures are brought into the contact state, and the cell structures are inserted into the rod-shaped member, a projection arranged along a circumference of the rod-shaped member to contact an end surface of the one end, and causing, at an end surface of the other end, a presser device to contact the end surface of the other end, a maturing step of cultivating and maturing the two or more cell structures by flowing a culture solution into the conduit of the rod-shaped member.

Advantageous Effects of Invention

According to the connection method and the connection support device of the present invention, in a case where a long cell structure is manufactured, it can be manufactured by creating and connecting a plurality of short cell structures.

DESCRIPTION OF EMBODIMENTS

Embodiment 1

Figure 1:
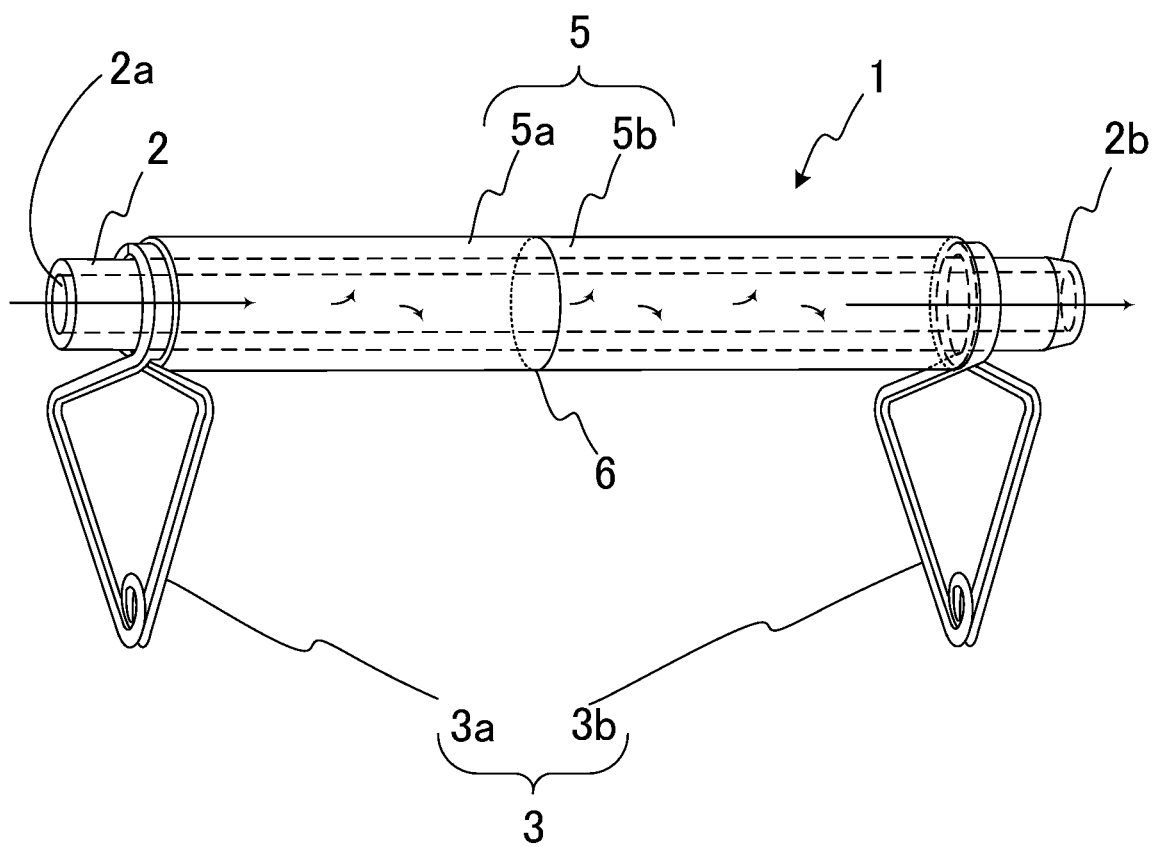
FIG. 1 is a diagram illustrating connection support devices and a connection method for cell structures in Embodiment 1 of the present invention.
Figure 2:
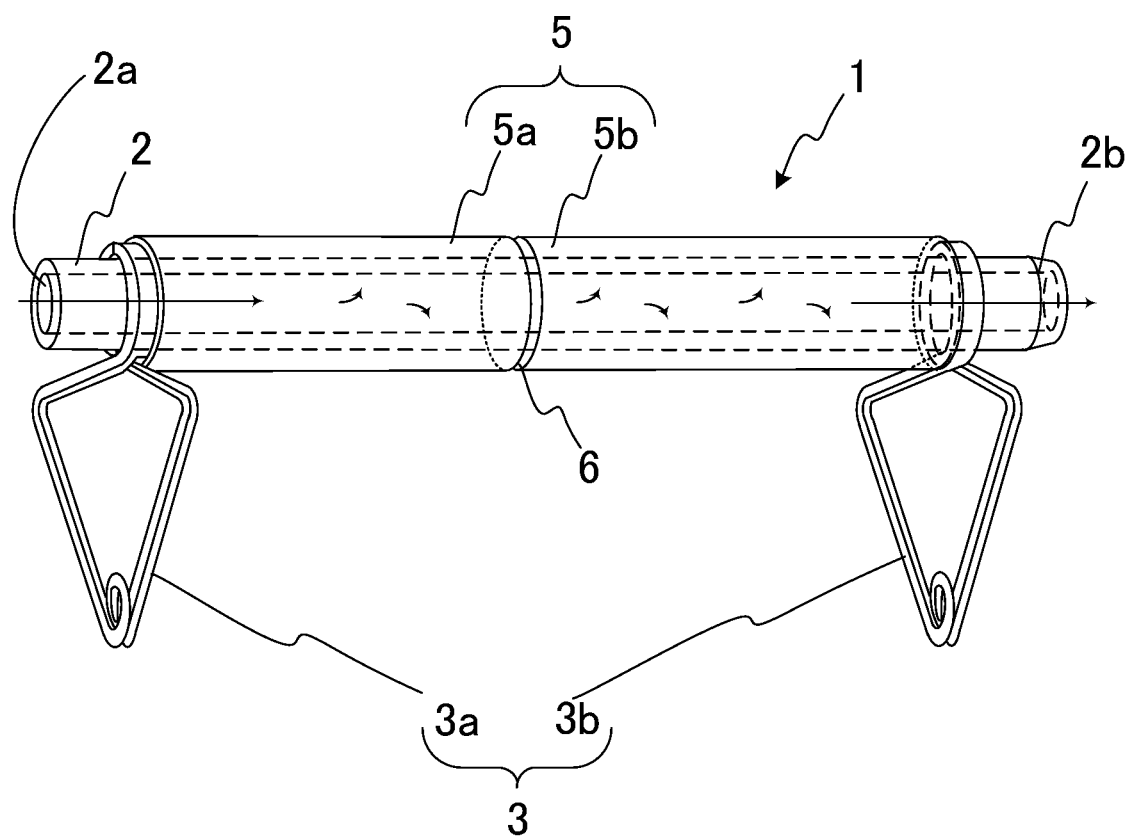
FIG. 2 is a diagram illustrating the connection support devices and the connection method for the cell structures in Embodiment 1 of the present invention, in a state where the cell structures have contracted.
Figure 3:
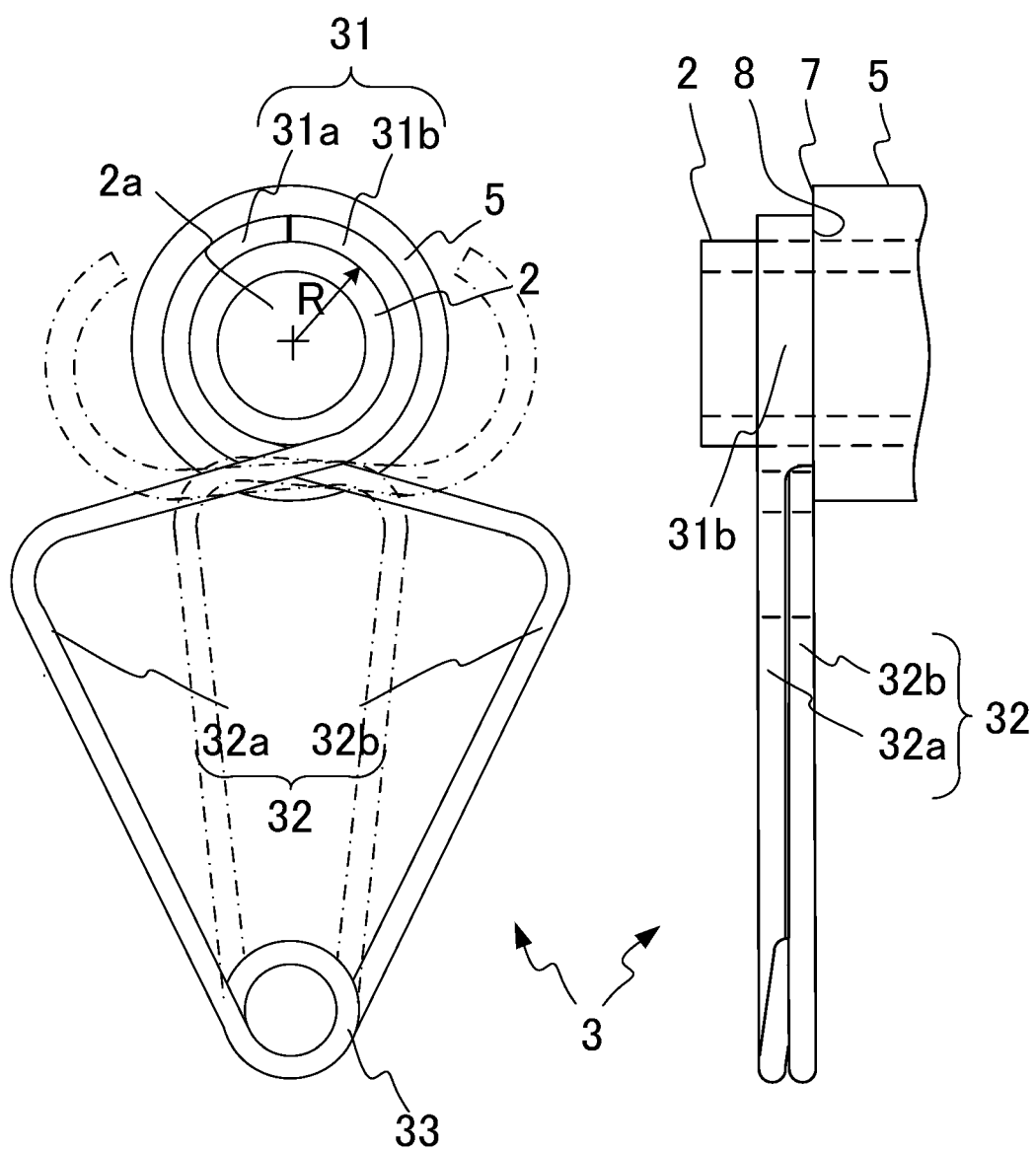
FIG. 3 is a diagram illustrating one embodiment of a presser device of the connection support device for the cell structure of the present invention.
Figure 4:
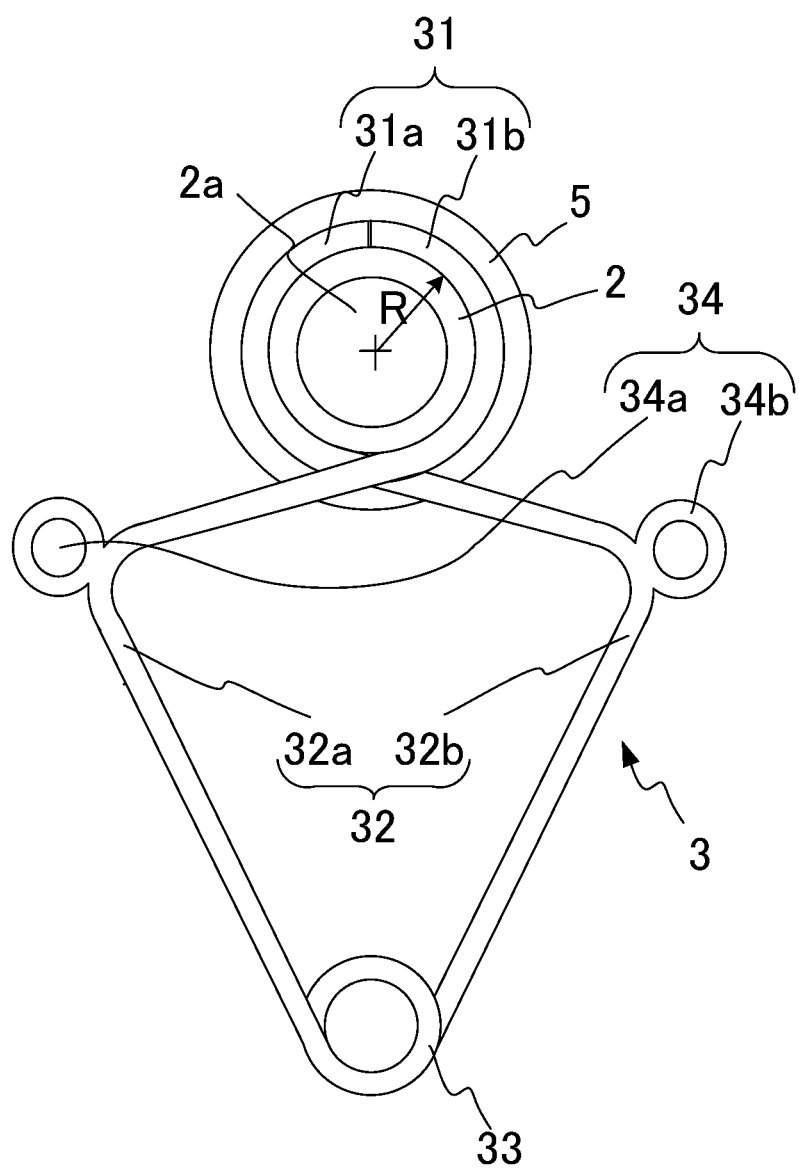
FIG. 4 is a diagram illustrating one embodiment of the presser device of the connection support device for the cell structure of the present invention.

First, using FIG. 1 to FIG. 4, a connection method for a cell structure 5 of the present invention and Embodiment 1 of a connection support device 1 for realizing it will be described. FIG. 1 illustrates the connection support device 1 to which two cell structures 5 are attached. FIG. 2 illustrates the state where bonding surfaces of the two cell structures 5 are separated, and a gap 6 is created. FIG. 3 is a diagram illustrating one embodiment of a presser device 3 constituting the connection support device 1. The left-hand diagram in FIG. 3 is a diagram seen from the axial direction of the cell structure 5, and the right-hand diagram in FIG. 3 is a diagram seen from the direction perpendicular to the left-hand side of FIG. 3. FIG. 4 is a diagram illustrating another embodiment of the presser device 3 constituting the connection support device 1.

Figure 7A:
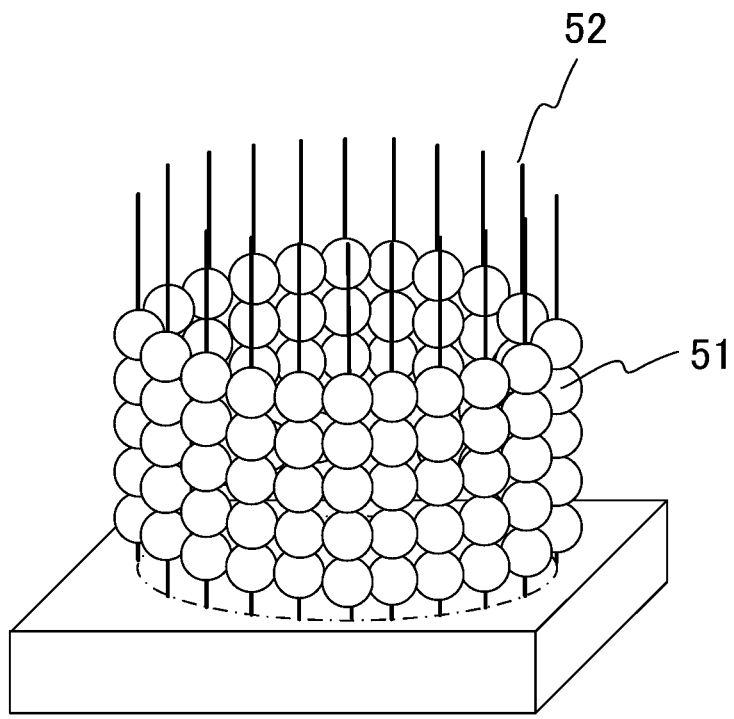
FIG. 7A is a schematic diagram illustrating the state where cell aggregates are stuck to needle-like bodies in the step of forming a cell structure.
Figure 7B:
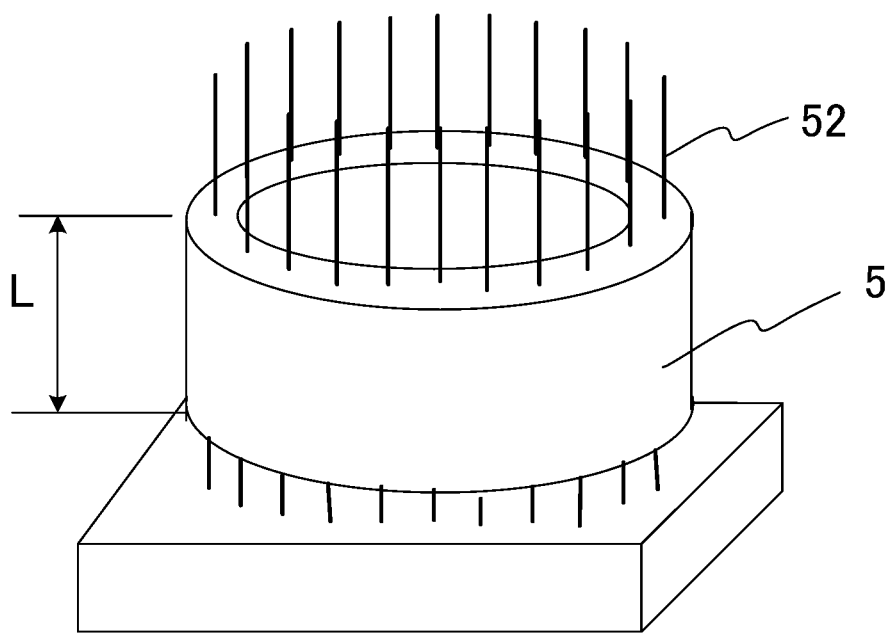
FIG. 7B is a schematic diagram illustrating the state where the adjacent cell aggregates are fused to each other to form the cell structure in the step of forming the cell structure.
Figure 7C:
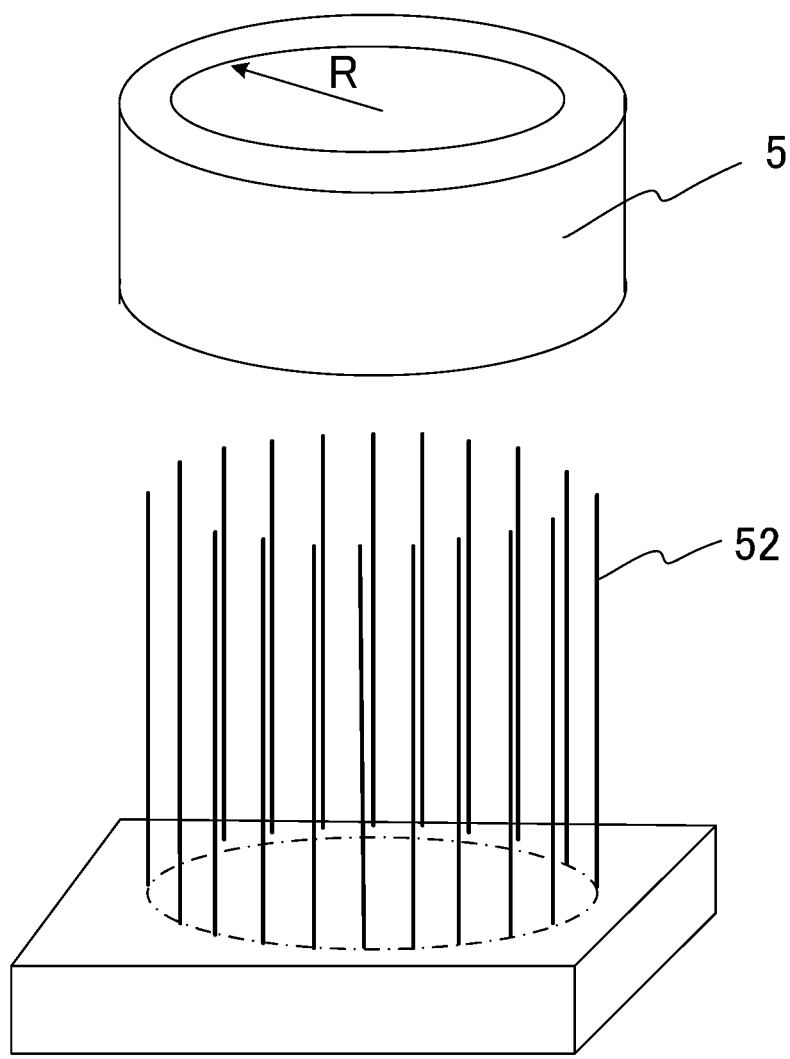
FIG. 7C is a schematic diagram illustrating the state showing the step of pulling out the formed cell structure from the needle-like bodies in the step of forming the cell structure.

The connection support device 1 includes a rod-shaped member 2 and the presser device 3. The cell structure 5 was formed in, for example, the steps of FIG. 7A to FIG. 7C and the step as described above, and has a tubular structure including a hollow portion having a circular cross section inside the cell structure 5. Here, a cell structure 5a and a cell structure 5b are prepared, and they are connected to each other. In this specification, it is assumed that the inner diameters of the cell structures 5a and 5b are R.

The rod-shaped member 2 is an elongated cylindrical member having a circular cross section. The outer diameter of the rod-shaped member 2 is R. In the step for connecting the cell structures 5a and 5b to each other, when the rod-shaped member 2 is inserted into the cell structures 5a and 5b, the inner diameters of the cell structures 5a and 5b are slightly larger than the outer diameter R of the rod-shaped member 2. However, since the inner diameters of the cell structures 5a and 5b have the characteristic of gradually contracting in the course of maturation of cells that constitute the cell structures 5a and 5b with the passage of time in the state where cultivation is being performed, when time elapses in the state where cultivation is being performed, the rod-shaped member 2 will be in the state where the rod-shaped member 2 is tightly inserted and fit into the cell structures 5a and 5b without a gap between the cell structures 5a and 5b and the rod-shaped member 2. In the inside, a conduit 2a is provided so as to penetrate along the axial direction in the longitudinal direction of the rod-shaped member 2 from one end to the other end of the rod-shaped member 2. As for the length of the rod-shaped member 2, the rod-shaped member 2 is longer than at least a combined total length of the cell structure 5a and the cell structure 5b. That is, when the rod-shaped member 2 is fit into in the hollow portions of the cell structure 5a and the cell structure 5b, even if one end of the cell structure 5a and one end of the cell structure 5b are in a contact state, the connected cell structures 5a and 5b are long enough to expose a certain amount of the rod-shaped member 2 at both ends of the connected cell structures 5a and 5b. A top end 2b of the rod-shaped member 2 has a tapered shape so as to be easily inserted into the hollow portion of the cell structure 5a.

The rod-shaped member 2 has a structure with oxygen permeability between the conduit 2a and the outer surface of the rod-shaped member 2. For example, small through-holes for oxygen penetration may be arranged between the conduit 2a and the outer surface of the rod-shaped member 2. Additionally, a material having oxygen permeability such as dimethylpolysiloxane (PDMS) may be used, without arranging the small through-holes for oxygen permeation. By introducing an oxygen-dissolved culture solution into the conduit 2a, as the culture solution passes, oxygen reaches the outer surface of the rod-shaped member 2, and the cell structure 5a can accept oxygen from the inner surface over the entire length of the cell structure 5a.

The presser device 3 includes a clamp portion 31 and a grip portion 32. The clamp portion 31 can be fixed to the rod-shaped member 2 by clamping and fitting to the rod-shaped member 2. The clamp portion 31 is divided into two portions, a fitting portion 31a and a fitting portion 31b, and when the fitting portion 31a and the fitting portion 31b are combined, a circular shape having the inner circumference radius of R is formed. The fitting portion 31a and the fitting portion 31b of the clamp portion 31 are coupled to an arm 32a and an arm 32b of the grip portion 32, respectively. The grip portion 32 includes a spring portion 33, and biases the grip portion 32, so that the arm 32a and the arm 32b are spread to combine the fitting portion 31a and the fitting portion 31b, and the inner circumference constitutes the circular shape having the inner circumference radius of R. In this state, the fitting portion 31a and the fitting portion 31b clamp the outer circumference of the rod-shaped member 2, and also fit to the rod-shaped member 2 (the state of solid lines in FIG. 3). By narrowing the arm 32a and the arm 32b, and applying force in the opposite direction to the bias direction of the grip portion 32, the fitting portion 31a and the fitting portion 31b are divided into two portions, and the fitting portion 31a and the fitting portion 31b are released from the state of clamping the rod-shaped member 2 (one-dot-chain lines in FIG. 3).

As illustrated in FIG. 3, in the state where the fitting portion 31a and the fitting portion 31b clamp the rod-shaped member 2, the fitting portion 31a and the fitting portion 31b close at an end surface 7 of an end of the cell structure 5a and the cell structure 5b, and a side surface 8 of the clamp portion 31 contacts the end surface 7. In this state, the presser devices 3 regulate at the both ends of the cell structure 5a and the cell structure 5b, so that the cell structure 5a and the cell structure 5b do not move on the rod-shaped member 2. At this time, ideally, as illustrated in FIG. 3, the presser device 3 has the structure in which the side surface 8 of the clamp portion 31 and the end surface 7 of each of the both ends of the cell structures 5a and 5b contact each other over the entire circumferences of the end surface 7. Especially, it is preferable that the side surface 8 of the clamp portion 31 of the presser device 3 is a flat surface. Accordingly, in the state where cultivation has advanced, the flatness of the end surface 7 of each of the both ends of the cell structures 5a and 5b becomes high. However, when the side surface 8 of the clamp portion 31 and the end surface 7 of each of the both ends of the cell structures 5a and 5b have the structures to at least partially contact each other, even if not contacting each other over the entire circumference of the end surface 7, as long as the presser device 3 can regulate at the both ends of the cell structure 5a and the cell structure 5b, so that the ends of the cell structure 5a and the cell structure 5b do not move on the rod-shaped member 2, an effect required for connection of the cell structures 5a and 5b is produced. Additionally, insertion holes 34a and 34b into which top ends 2b of tweezers can be inserted can be arranged in the arms 32a and 32b, respectively, so that the arms 32a and 32b of the presser device 3 can be expanded and narrowed with the tweezers (FIG. 4).

Subsequently, how to connect the cell structure 5a and the cell structure 5b to each other by using the connection support device 1, a cell structure connection method in Embodiment 1, will be described. First, the rod-shaped member 2 is inserted into the hollow portions of the cell structure 5a and the cell structure 5b (insertion step). Subsequently, a contact state is made so that there is no gap 6 between the opposing ends of the cell structure 5a and the cell structure 5b. In this state, the rod-shaped member 2 is clamped by the two presser devices 3a and 3b at the both ends of the cell structure 5a and the cell structure 5b that are not in a contact state, and the presser device 3a and the presser device 3b are made to fit to the rod-shaped member 2. At this time, the cell structures 5a and 5b are fixed by clamping the rod-shaped member 2 with the two presser devices 3a and 3b, at the positions where the respective side surfaces 8 of the two presser devices 3a and 3b contact the end surfaces 7 of the both ends of the cell structures 5a and 5b, and pressing forces are applied in directions along which the cell structures 5a and 5b relatively approach to the end surfaces of the cell structures 5a and 5b in the contact state, respectively (fixing step).

Figure 5:
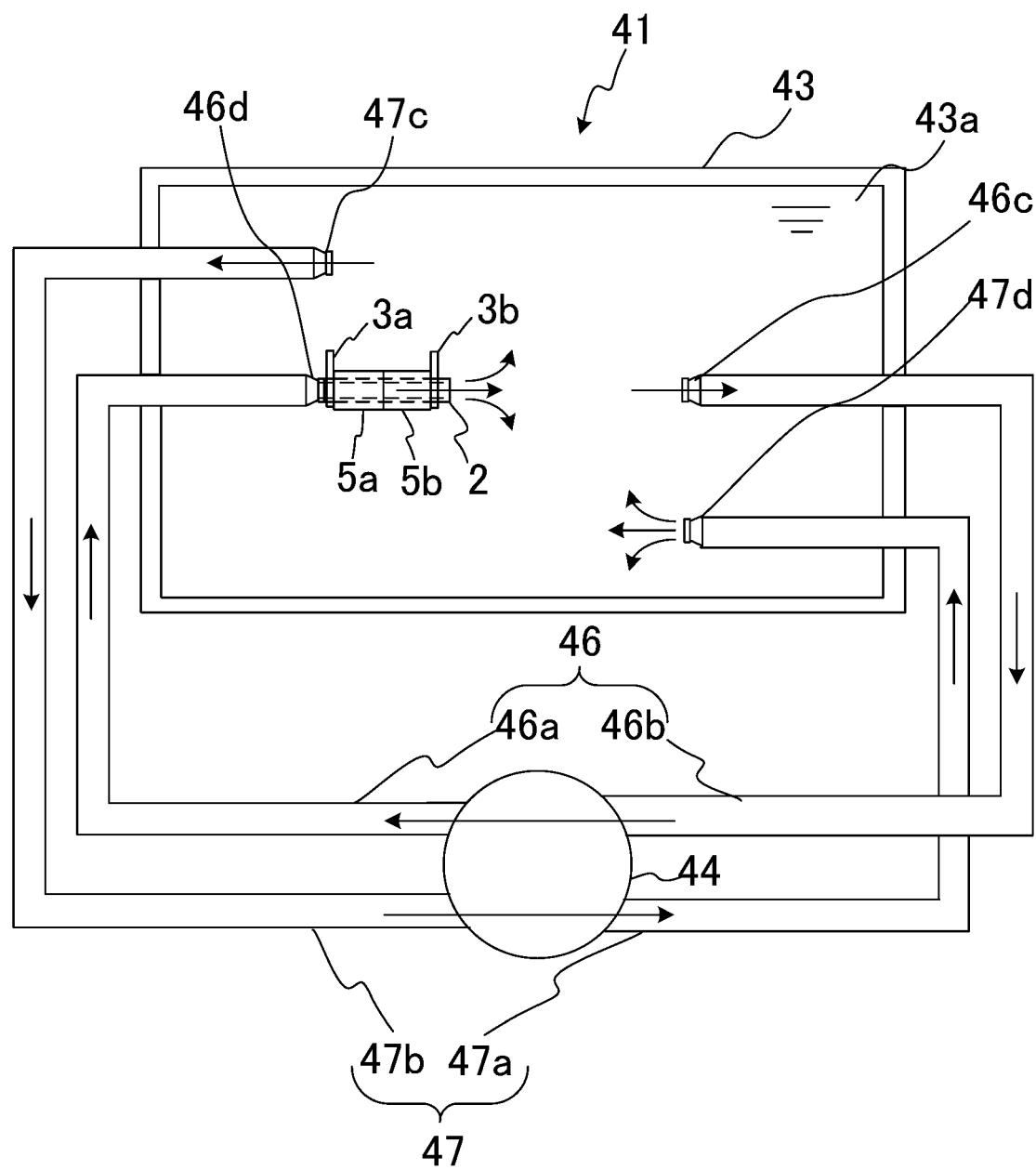
FIG. 5 is a diagram illustrating a cultivation apparatus for attaching the cell structure to which the connection support devices are attached, when connecting the cell structures in the present invention.

In this state, a solution allowing permeation of oxygen is passed through the inside of the conduit 2a of the rod-shaped member 2, and the inside and outside of the cell structures 5a and 5b are immersed in the solution, and cultured and matured for a predetermined time period (maturing step). Referring to FIG. 5, an example of using a cultivation maintaining apparatus 41 will be described as an example of supplying a culture solution to the rod-shaped member 2 inserted into the cell structures 5a and 5b in the maturing step. FIG. 5 is a schematic diagram of the cultivation maintaining apparatus 41. The cultivation maintaining apparatus 41 includes a sealed culture chamber 43, and the inside is filled with a culture solution 43a. The culture chamber 43 includes a first inlet 46d and a second inlet 47d for introduction into the culture chamber 43, and a first exit 46c and a second exit 47c for discharging the culture solution 43a from the culture chamber 43. Additionally, the cultivation maintaining apparatus 41 includes a first conduit 46 that fluidly connects the first exit 46c to the first inlet 46d via a pump 44, and a second conduit 47 that fluidly connects the second exit 47c to the second inlet 47d via the pump 44. The second inlet 47d, the first exit 46c, and the second exit 47c are open ends, and the rod-shaped member 2 is attached to the first inlet 46d via an adapter.

The culture solution 43a flows back inside the first conduit 46 and the second conduit 47 with the driving force of the pump 44. When the culture chamber 43 filled with the culture solution 43a is seen as a starting point, the culture solution 43a flows out of the first exit 46c into a first conduit 46b, and travels toward the pump 44. Additionally, the culture solution 43a flows out of the second exit 47c into a second conduit 47b, and travels toward the pump 44. Thereafter, the culture solution 43a to which required nutrients and oxygen have been supplied at the pump 44 returns to the culture chamber 43 from the first conduit 46a via the first inlet 46d with the driving force of the pump 44. Additionally, it returns to the culture chamber 43 from the second conduit 47a via the second inlet 47d. The first conduit 46 is mainly for supplying the culture solution 43a to the inside of the cell structures 5a and 5b through a penetration conduit inside the rod-shaped member 2. Additionally, the second conduit 47 is mainly for spreading the culture solution 43a over the outside of the cell structures 5a and 5b. By circulating the culture solution 43a within the cultivation maintaining apparatus 41 for a predetermined time period, the cell structures 5a and 5b are cultivated and matured.

Since the cell structures 5a and 5b contract in the axial direction of the rod-shaped member 2 with the progress of the maturing step, the pressing forces at the end surfaces of the cell structures 5a and 5b in the contact state are decreased, and in some cases, the end surfaces in the contact state may be separated to create the gap 6. In that case, the distance of each of the two presser devices 3a and 3b is reduced to brought the separated gap 6 into the contact state again, and the rod-shaped member 2 is pressed and clamped again by the two presser devices 3a and 3b at the positions where the pressing forces are maintained at the end surfaces of the cell structures 5a and 5b in the contact state.

With the completion of the maturing step in which the cells of the cell structures 5a and 5b mature through cultivation for a predetermined time period, the cells at the portions of the cell structures 5a and 5b in the contact state are fused to each other, and the cell structures 5a and 5b are connected to each other.

Embodiment 2

Figure 6:
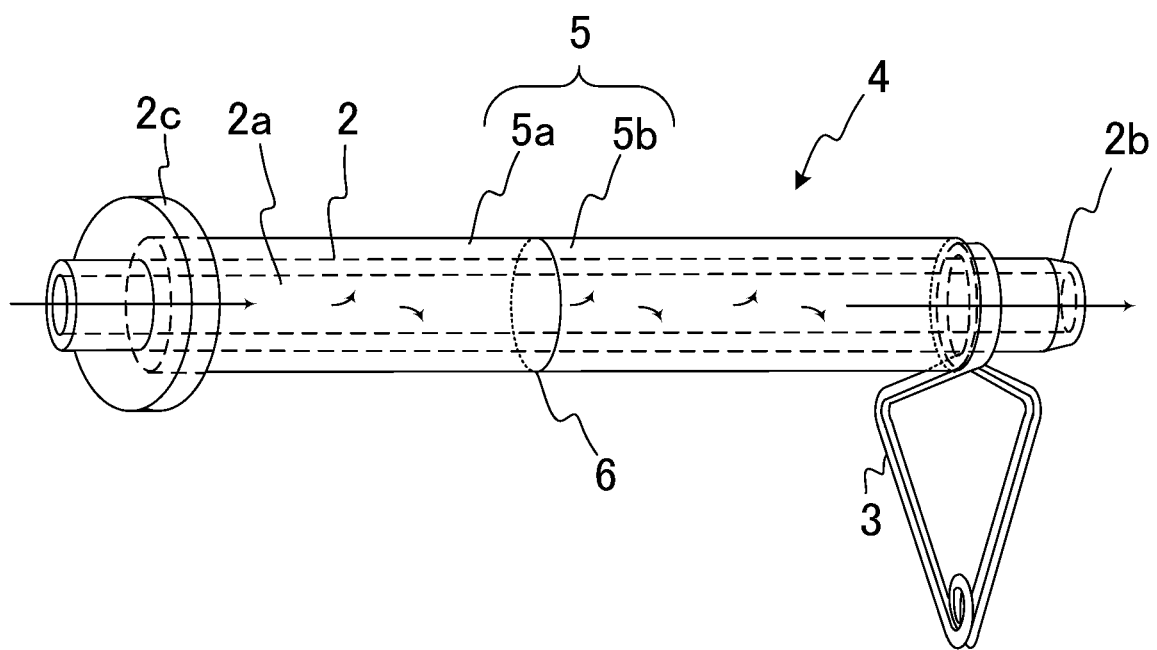
FIG. 6 is a diagram illustrating a connection support device and a connection method for cell structures in Embodiment 2 of the present invention.

Subsequently, using FIG. 6, a connection method for the cell structure 5 of the present invention and Embodiment 2 of the connection support device 1 for realizing it will be described. In Embodiment 1, the two presser devices 3a and 3b are used. A connection support device 4 of Embodiment 2 is different in that the rod-shaped member 2 and one presser device 3 are used to connect the cell structures 5a and 5b to each other. Hereinafter, regarding Embodiment 2, the differences from Embodiment 1 will be described. FIG. 6 is a diagram illustrating the connection support device 4 and the connection method for the cell structure in Embodiment 2 of the present invention.

In the rod-shaped member 2 of Embodiment 2, a projection 2c is arranged in the vicinity of an end of the rod-shaped member 2 opposite to the tapered top end 2b. The projection 2c has a flange-shape arranged to project in the radial direction of the rod-shaped member 2 along the circumference of the rod-shaped member 2 in the vicinity of its end. The radial distance is greater than the thicknesses of the cell structure 5a and the cell structure 5b, and an end of the cell structure 5a can be made to abut against the projection 2c. In the other respects, the rod-shaped member 2 is the same as in Embodiment 1. The presser device 3 of Embodiment 2 is completely the same as in Embodiment 1 as illustrated in FIG. 3 and FIG. 4. However, although the two presser devices 3a and 3b are required in Embodiment 1, only one presser device 3 is used in Embodiment 2.

Subsequently, how to connect the cell structure 5a and the cell structure 5b to each other by using the connection support device 4, a cell structure connection method in Embodiment 2, will be described. First, the rod-shaped member 2 is inserted into the hollow portions of the cell structure 5a and the cell structure 5b (insertion step). Then, a contact state is made so that there is no gap 6 between the opposing ends of the cell structure 5a and the cell structure 5b. At this time, an end surface of the cell structure 5a is made to abut against the projection 2c. The order of the step of making the contact state so that there is no gap between the opposing ends of the cell structure 5a and the cell structure 5b, and the step of making the end surface of the cell structure 5a to abut against the projection 2c does not matter.

In the state where the end surface of the cell structure 5a abuts against the projection 2c, the rod-shaped member 2 is clamped by the presser device 3 at the end of the cell structure 5b that is not in the contact state to make the presser device 3 fit to the rod-shaped member 2. At this time, the cell structures 5a and 5b are fixed by clamping the rod-shaped member 2 with the presser device 3 at the position where the side surface of the presser device 3 contacts the end surface of the end of the cell structure 5b, and a pressing force is applied in a direction along which each of the cell structures 5a and 5b relatively approaches to the end surface of the cell structure 5b in the contact state (fixing step). Then, the end surface of the cell structure 5a on the side opposite to the presser device 3 abuts and is pressed against the projection 2c. As a result, the end surfaces of the cell structures 5a and 5b in the contact state are pressed against each other.

In this state, a solution allowing permeation of oxygen is passed through the inside of the conduit 2a of the rod-shaped member 2, and the inside and outside of the cell structures 5a and 5b are immersed in the solution, and cultured and matured for a predetermined time period (maturing step). The maturing step is performed in the same apparatus as illustrated in FIG. 5 of Embodiment 1. Since the cell structures 5a and 5b contract in the axial direction of the rod-shaped member 2 with the progress of the maturing step, the pressing forces at the end surfaces of the cell structures 5a and 5b in the contact state are decreased, and in some cases, the end surfaces in the contact state may be separated to create the gap 6. In that case, as in Embodiment 1, the presser device 3 is moved closer to the projection 2c to bring the separated gap 6 into the contact state again, and the rod-shaped member 2 is pressed and clamped again by the presser device 3 at the position where the pressing forces are maintained at the end surfaces of the cell structures 5a and 5b in the contact state.

With the completion of the maturing step in which the cells of the cell structures 5a and 5b mature through cultivation for a predetermined time period, the cells at the portions of the cell structures 5a and 5b in the contact state are fused to each other, and the cell structures 5a and 5b are connected to each other.

REFERENCE SIGNS LIST 1, 4 connection support device, 2 rod-shaped member, 3 presser device, 5 cell structure, 6 gap, 2c projection, 31 clamp portion, 31a, 31b fitting portion, 32 grip portion, 32a, 32b arm, 33 spring portion, 34a, 34b insertion hole, 41 cultivation maintaining apparatus, 43 culture chamber

The invention claimed is:

1. A connection support device capable of connecting two or more tubular cell structures, each of the tubular cell structures having an inner hollow portion, the connection support device comprising:
   a rod-shaped member insertable into the hollow portion of said two or more tubular cell structures, the rod-shaped member including a circular cross section having an outer diameter, wherein said outer diameter is closely contactable to inner surfaces of the tubular cell structures by shrinkage of the tubular cell structures, and said rod-shaped member having a total length longer than a sum of respective lengths of the two or more tubular cell structures, wherein the rod-shaped member is made of a material with oxygen permeability;
   a presser device including a clamp portion capable of being fixed onto the rod-shaped member by clamping an outer peripheral surface of the rod-shaped member with the clamp portion to fit an inner surface of the clamp portion to the outer peripheral surface of the rod-shaped member; and
   a movement stopping feature positioned to be contacted with one end of the two or more tubular cell structures, and being capable of preventing said tubular structures from moving on said rod-shaped member,
   wherein when the rod-shaped member is inserted into the two or more tubular cell structures in a state where ends of the two or more tubular cell structures contact with each other, the clamp portion makes contact with a surface of a first end of the two or more tubular cell structures and the movement stopping feature makes contact with a surface of a second end opposite to the first end of the two or more tubular cell structures.

2. A connection support device according to claim 1, wherein the movement stopping feature is another presser device including a clamp portion capable of being fixed onto the rod-shaped member by clamping an outer peripheral surface of the rod-shaped member with the clamp portion to fit an inner surface of the clamp portion to the outer peripheral surface of the rod-shaped member, the clamp portion of the another pressor device being to contact the surface of the second end of the two or more tubular cell structures.

3. A connection support device according to claim 1, wherein the movement stopping feature is
   a projection provided on the rod shaped member, wherein when the rod-shaped member is inserted into the two or more tubular cell structures in a state where the ends of the two or more tubular cell structures contact with each other, the projection arranged along a circumference contacting the surface of the second end of the two or more tubular cell structures.

4. A connection support device according to claim 2 or 3, wherein the clamp portion of the presser device has an inner diameter almost the same as the outer diameter of the cross section of the rod-shaped member.

5. A connection support device according to claim 2 or 3, wherein the material with oxygen permeability is dimethylpolysiloxane.

6. A connection support device according to claim 5, wherein the rod-shaped member includes a conduit capable of having a culture solution flow therethrough along an axial direction of the rod-shaped member from one end to the other end of the rod-shaped member.

7. A connection support device according to claim 2 or 3, wherein the contact between the each of the clamp portions and the each of the surfaces of the first and second ends of the tubular cell structures is an entire circumference contact of the first and second ends of two or more tubular cell structures.

8. A connection support device according to claim 2 or 3, wherein the contact between the each of the clamp portion and the each of the surfaces of the first and second ends is a partial contact of at least a part of the each of the first and second ends of the two or more tubular cell structures.

9. A cell structure connection method for connecting two or more tubular cell structures by using a connection support device according to claim 1
   wherein the cell structure connection method comprises:
   an insertion step of inserting the rod-shaped member into the hollow portion of each of the two or more tubular cell structures;
   a fixing step of fixing the two or more tubular cell structures to the rod-shaped member with presser device and the movement stopping feature so that the presser device contacts the first end and the movement stopping feature contacts the second end of the two or more tubular cell structures,
   a maturing step of cultivating and maturing the two or more tubular cell structures by flowing a culture solution into a conduit of the rod-shaped member along an axial direction of the rod-shaped member from one end to the other end of the rod-shaped member.

10. A cell structure connection method according to claim 9, wherein the movement stopping feature is another presser device including a clamp portion capable of being fixed onto the rod-shaped member by clamping an outer peripheral surface of the rod-shaped member with the clamp portion to fit an inner surface of the clamp portion to the outer peripheral surface of the rod-shaped member.

11. A cell structure connection method for connecting two or more tubular cell structures according to claim 9,
   wherein the movement stopping feature is:
   a projection provided on the rod shaped member wherein when the rod-shaped member is inserted into the two or more tubular cell structures in a state where the ends of the two or more tubular cell structures contact with each other, the projection is arranged along a circumference contacting the surface of the second end of the two or more tubular cell structures.

12. A cell structure connection method according to claim 10 or 11, wherein the fixing step comprises a step of bringing, when portions of the two or more tubular cell structures in the contact state are separated, the portions into the contact state again, and fixing the tubular cell structures to the rod-shaped member by causing, at the second end of the tubular cell structures, the projection of the rod-shaped member to contact the surface of the second end, and causing, at the surface of the first end, the presser device to contact the surface of the first end.

13. A cell structure connection method according to claim 10 or 11, wherein the maturing step includes a step in which the hollow portions of the two or more tubular cell structures contract, and the hollow portions closely contact an outer circumference surface of the rod-shaped member.

14. A cell structure connection method according to claim 10 or 11, wherein the material with oxygen permeability is dimethylpolysiloxane.

\* \* \* \* \*